United States Patent
Bedoukian et al.

(10) Patent No.: US 9,701,609 B2
(45) Date of Patent: Jul. 11, 2017

(54) PERFUME COMPOSITIONS CONTAINING ISOMERIC ALKADIENALS

(71) Applicant: BEDOUKIAN RESEARCH, INC., Danbury, CT (US)

(72) Inventors: Robert H. Bedoukian, West Redding, CT (US); Krzysztof Swierczek, Danbury, CT (US); Douglas Jay Pesak, Oxford, CT (US); Hifzur R. Ansari, Old Tappen, NJ (US)

(73) Assignee: Bedoukian Research, Inc., Danbury, CT (US)

(*) Notice: Subject to any disclaimer, the term of this patent is extended or adjusted under 35 U.S.C. 154(b) by 3 days.

(21) Appl. No.: 14/830,262

(22) Filed: Aug. 19, 2015

(65) Prior Publication Data

US 2016/0052855 A1    Feb. 25, 2016

Related U.S. Application Data

(60) Provisional application No. 62/039,661, filed on Aug. 20, 2014.

(51) Int. Cl.
  *C07C 47/21* (2006.01)
  *C11B 9/00* (2006.01)

(52) U.S. Cl.
  CPC .......... *C07C 47/21* (2013.01); *C11B 9/0015* (2013.01)

(58) Field of Classification Search
  CPC .............................. C11B 9/0015; C07C 47/21
  See application file for complete search history.

(56) References Cited

U.S. PATENT DOCUMENTS 3,686,003 A    8/1972   Van Dorp et al.
3,821,421 A *  6/1974   Begemann et al. ............ A23L 27/2024
                                                            426/534

(Continued)

OTHER PUBLICATIONS

International Search Report dated Nov. 19, 2015 from corresponding International Application No. PCT/US15/45894, 3 pages.

(Continued)

*Primary Examiner* — Lanee Reuther
(74) *Attorney, Agent, or Firm* — Ohlandt, Greeley, Ruggiero & Perle, L.L.P.

(57) ABSTRACT

A perfume composition comprising an effective amount of at least one alkadienal selected from 4,8-undecadienal and isomers thereof, 4,9-dodecadienal and isomers thereof, and 4,10-tridecadienal and isomers thereof. The isomers of 4,8-undecadienal comprise Z,Z-4,8-undecadienal, E,E-4,8-undecadienal, and mixed Z/E isomers of 4,8-undecadienal; the isomers of 4,9-dodecadienal comprise Z,Z-4,9-dodecadienal, E,E-4,9-dodecadienal, and mixed Z/E isomers of 4,9-dodecadienal; and the isomers of 4,10-tridecadienal comprise Z,Z-4,10-tridecadienal, E,E-4,10-tridecadienal, and mixed Z/E isomers of 4,10-tridecadienal. A composition comprising an effective amount of at least one alkadienal selected from 4,8-undecadienal and isomers thereof, 4,9-dodecadienal and isomers thereof, and 4,10-tridecadienal and isomers thereof. Processes for the preparation of the isomer mixtures of alkadienals are provided. The isomeric alkadienals have a range of fresh, watery, ozone, grapefruit, tangerine, orange peel, aldehydic notes of exceptional strength.

14 Claims, 1 Drawing Sheet

| Material | Odor Description | Strength Scale= 0 -10 (5 panelists) |
|---|---|---|
| Z,Z-4,7-decadienal | very aldehydic, fatty, calamus-like, somewhat chemical | 6 |
| Z,Z-4,8-undecadienal | Powerful, diffusive, green, watery, ozonic, citrus, grapefruit, sun dried linen | 8 |
| Mixed (Z & E)4,8-undecadienal | Very strong, aldehydic, sea side clean, green, watery | 10 |
| Z,Z-4,9-dodecadienal | Strong, fresh, aldehydic, floral, tangerine/mandrine note, shades of rose and muguet | 10 |
| Mixed (Z&E)4,9-dodecadienal | Very strong, fresh, citrus, aldehydic | 8 |
| Z,Z-4,10-tridecadienal | Ozonic, orange peel (white pith), somewhat fatty | 8 |
| Mixed (Z&E)4,10-tridecadienal | Ozonic, aldehyde, green | 6 |

(56) References Cited

U.S. PATENT DOCUMENTS

| | | | |
|---|---|---|---|
| 3,920,752 A | 11/1975 | Lamparsky | |
| 3,928,402 A | 12/1975 | Naf | |
| 4,687,599 A * | 8/1987 | Van Lier | C07C 45/515 512/27 |
| 2001/0015422 A1 | 8/2001 | Wachtler et al. | |
| 2001/0053372 A1 * | 12/2001 | Ishino | A01N 35/02 424/400 |
| 2012/0052177 A1 * | 3/2012 | Takakura | A23L 1/22621 426/535 |
| 2014/0120232 A1 * | 5/2014 | Haraguchi | A23L 1/22075 426/534 |

OTHER PUBLICATIONS

Written Opinion dated Nov. 19, 2015 from corresponding International Application No. PCT/US15/45894, 10 pages.

Ujvary I. et al., "Simple and economic syntheses of some (Z)-7-alkenyl and (Z)-9-alkenyl acetates, and of (E,Z)-7, 9-dodecadien-1-yl acetate, the sex-pheromone of the European grapevine moth, using aleuritic acid as a common starting material", Journal of Chemical Ecology, 1985, vol. 11(1), pp. 113-124; especially p. 116, 119, 122-123, 12 pages.

Delort et al.; "Identification and Synthesis of New Volatile Molecules Found in Extracts Obtained from Distinct Parts of Cooked Chicken"; Journal of Agricultural and Food Chemistry; 2011, 59, pp. 11752-11763.

Mosciano et al.; "Organoleptic Characteristics of Flavor Materials"; Perfumer & Flavorist, vol. 23, May/Jun. 1998, pp. 55-57.

International Preliminary Report on Patentability dated Dec. 5, 2016, 8 pages.

* cited by examiner

| Material | Odor Description | Strength Scale= 0 -10 (5 panelists) |
|---|---|---|
| Z,Z-4,7-decadienal | very aldehydic, fatty, calamus-like, somewhat chemical | 6 |
| Z,Z-4,8-undecadienal | Powerful, diffusive, green, watery, ozonic, citrus, grapefruit, sun dried linen | 8 |
| Mixed (Z & E)4,8-undecadienal | Very strong, aldehydic, sea side clean, green, watery | 10 |
| Z,Z-4,9-dodecadienal | Strong, fresh, aldehydic, floral, tangerine/mandrine note, shades of rose and muguet | 10 |
| Mixed (Z&E)4,9-dodecadienal | Very strong, fresh, citrus, aldehydic | 8 |
| Z,Z-4,10-tridecadienal | Ozonic, orange peel (white pith), somewhat fatty | 8 |
| Mixed (Z&E)4,10-tridecadienal | Ozonic, aldehyde, green | 6 |

PERFUME COMPOSITIONS CONTAINING ISOMERIC ALKADIENALS

RELATED APPLICATION

This application claims the benefit of copending U.S. Application No. 62/039,661, filed Aug. 20, 2014, which is incorporated herein by reference in its entirety.

BACKGROUND OF THE DISCLOSURE

1. Field of the Disclosure

This disclosure relates to isomeric alkadienals and their use in perfume compositions. In particular, this disclosure relates to isomeric undecadienals, dodecadienals and tridecadienals and their use in perfume compositions. More, in particular, this disclosure provides cis- and trans-isomers of 4,8-undecadienal, 4,9-dodecadienal and 4,10-tridecadienal for use in perfumery applications.

2. Description of the Related Art

Various alkenals and alkadienals having 10 or more carbon atoms are known as fragrance materials or flavorings. For example, S. Arctander in "Perfume and Flavor Chemicals", names 2,4-decadienal and 2-decenal as fragrance materials but without any reference to cis or trans configuration, and 8-, 9- and 10-undecenal, of which 8- and 9-undecenal have the cis configuration. In U.S. Pat. Nos. 3,821,421 and 3,686,003, it is reported that both cis-4-decenal and cis, cis-4,7-tridecadienal and other polyunsaturated aldehydes containing 11-17 carbon atoms are suitable for imparting an aroma of chicken meat to foodstuffs.

Other dienals such as 2E,4E-decadienal, 2E,4E-undecadienal and 2E,6Z-dodecadienal have been reported and used in chicken meat flavor preparations. Further to this, Gerard Moschiano (Perfumer & Flavorist 23, No. 3, 55, 1998) describes the alkyl dienal, 2,4-decadienal as having fatty, chicken, fried, citrus, coriander and brothy odor. More recently, Delort et al reported the identification and synthesis of several alkadienals found in extracts obtained from distinct parts of chicken (J. Agric. Food Chem. 2011, 59, 11752-11763). For this reason, it was not to be expected that this class of compounds would be suitable as raw materials for perfume compositions.

In U.S. Pat. No. 3,928,402, a method of synthesis is described for γ-δ-unsaturated carbonyl compounds including aldehydes. However, only compounds with a 2,4-diene system and/or an ester or keto group are disclosed.

In U.S. Pat. No. 3,920,752, it is reported that certain γ-δ-unsaturated aldehydes are valuable fragrance materials. From the structural formulae, however, only branched C-11 dienals with a trans-double bond at carbon 4 are disclosed. In U.S. Pat. No. 4,687,599, it is reported that cis,cis-4,7-decadienal, cis,cis-4,7,9-decatrienal and 4,7,12-tridecatrienal are useful fragrance materials but the trans-isomers are excluded.

None of these publications give any indication that in particular the geometric isomers of 4,8-undecadienal, 4,9-dodecadienal and 4,10-tridecadienal would be suitable ingredients for perfume formulations.

There is an ongoing interest in the fragrance industry to use new compounds that enhance or improve odor character and impart new notes to help perfumers create exciting new fragrance experience desired by consumers.

The present disclosure provides many advantages, which shall become apparent as described below.

SUMMARY OF THE DISCLOSURE

This disclosure provides isomeric alkadienals and their use in perfume compositions. In particular, this disclosure provides isomeric undecadienals, dodecadienals and tridecadienals and their use in perfume compositions. More, in particular, this disclosure provides cis- and trans-isomers of 4,8-undecadienal, 4,9-dodecadienal and 4,10-tridecadienal for use in perfumery applications.

This disclosure relates to the preparation of alkadienals and their use in fragrance formulations. These new materials have a range of fresh, watery, ozone, grapefruit, tangerine, orange peel, aldehydic notes highly desirable in creating consumer acceptable fragrances. Additionally, these materials are extremely cost effective since they possess high odor intensity and can be effective at imparting the desirable odor contribution to a fragrance at a very low concentration.

This disclosure also relates in part to a perfume composition comprising an effective amount of at least one alkadienal selected from 4,8-undecadienal and isomers thereof, 4,9-dodecadienal and isomers thereof, and 4,10-tridecadienal and isomers thereof. The isomers of 4,8-undecadienal comprise Z,Z-4,8-undecadienal, E,E-4,8-undecadienal, and mixed Z/E isomers of 4,8-undecadienal; the isomers of 4,9-dodecadienal comprise Z,Z-4,9-dodecadienal, E,E-4,9-dodecadienal, and mixed Z/E isomers of 4,9-dodecadienal; and the isomers of 4,10-tridecadienal comprise Z,Z-4,10-tridecadienal, E,E-4,10-tridecadienal, and mixed Z/E isomers of 4,10-tridecadienal.

This disclosure further relates in part to a composition comprising an alkadienal selected from 4,8-undecadienal and isomers thereof, 4,9-dodecadienal and isomers thereof, and 4,10-tridecadienal and isomers thereof. The isomers of 4,8-undecadienal comprise Z,Z-4,8-undecadienal, E,E-4,8-undecadienal, and mixed Z/E isomers of 4,8-undecadienal; the isomers of 4,9-dodecadienal comprise Z,Z-4,9-dodecadienal, E,E-4,9-dodecadienal, and mixed Z/E isomers of 4,9-dodecadienal; and the isomers of 4,10-tridecadienal comprise Z,Z-4,10-tridecadienal, E,E-4,10-tridecadienal, and mixed Z/E isomers of 4,10-tridecadienal. The composition can be a fragrance composition or a flavor composition.

This disclosure yet further relates in part to process comprising reacting an isomeric alkenal compound with a derivative of an alkyltriphenylphosphonium halide compound under reaction conditions sufficient to form an isomer mixture of a derivatized alkadiene compound. The isomer mixture of the derivatized alkadiene compound is then reacted under reaction conditions sufficient to form an alkadienal compound. The alkadienal compound is selected from the group consisting 4,8-undecadienal and isomers thereof, 4,9-dodecadienal and isomers thereof, and 4,10-tridecadienal and isomers thereof.

This disclosure also relates in part to process comprising reacting a derivative of an isomeric alkadiene compound in the presence of an isomerizing agent under reaction conditions sufficient to form an isomer mixture of the derivative of the alkadiene compound. The isomer mixture of the derivative of the alkadiene compound is then reacted in the presence of a reducing agent under reaction conditions sufficient to form an isomer mixture of an alkadienal compound. The alkadienal is selected from the group consisting 4,8-undecadienal and isomers thereof, 4,9-dodecadienal and isomers thereof, and 4,10-tridecadienal and isomers thereof.

This disclosure further relates in part to an alkadienal compound selected from 4,8-undecadienal and isomers thereof, 4,9-dodecadienal and isomers thereof, and 4,10-tridecadienal and isomers thereof. In an embodiment, the alkadienal compound is the same alkadienal in the compositions and perfume compositions of this disclosure.

The cis- and trans-isomers of 4,8-undecadienal, 4,9-dodecadienal and 4,10-tridecadienal of this disclosure surprisingly possess extremely desirable odor character and a very low threshold of odor perception, resulting in high odor intensity when added to fragrance compositions. The high odor strength of these dienal isomers is an attribute that allows perfumers to use trace quantities of these materials to achieve high odor impact at a low cost.

Further objects, features and advantages of the present disclosure will be understood by reference to the following drawings and detailed description.

BRIEF DESCRIPTION OF THE DRAWINGS

FIG. 1 lists odor description and strength for Z,Z-4,7-decadienal, Z,Z-4,8-undecadienal, mixed (Z & E) 4,8-undecadienal, Z,Z-4,9-dodecadienal, mixed (Z & E) 4,9-dodecadienal, Z,Z-4,10-tridecadienal and mixed (Z & E) 4,10-tridecadienal.

DESCRIPTION OF THE PREFERRED EMBODIMENTS

This disclosure provides isomeric alkadienals and their use in perfume compositions. In particular, this disclosure provides isomeric undecadienals, dodecadienals and tridecadienals and their use in perfume compositions. More, in particular, this disclosure provides cis- and trans-isomers of 4,8-undecadienal, 4,9-dodecadienal and 4,10-tridecadienal for use in perfumery applications.

The isomeric undecadienals, dodecadienals and tridecadienals of this disclosure have a range of fresh, watery, ozone, grapefruit, tangerine, orange peel, aldehydic notes of exceptional strength.

Illustrative alkadienals of this disclosure are represented by the formulas set for below:

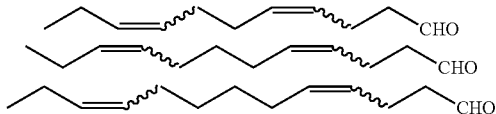

The isomeric alkadienals of this disclosure have a Z/E isomer ratios of their double bonds of from about 30:1 to about 1:30, or from about 12:1 to about 1:12, or from about 9:1 to about 1:9.

The isomeric alkadienal composition has from about 0 percent to about 100 percent of Z,Z isomers, or from about 5 percent to about 95 percent of Z,Z isomers, or from about 20 percent to about 90 percent of Z,Z isomers, or from about 30 percent to about 85 percent of Z,Z isomers, based on the total Z and E isomers in the composition.

The isomeric alkadienal composition has from about 0 percent to about 100 percent of Z,E isomers, or from about 0.5 percent to about 90 percent of Z,E isomers, or from about 1 percent to about 30 percent of Z,E isomers, or from about 2 percent to about 20 percent of Z,E isomers, based on the total Z and E isomers in the composition.

The isomeric alkadienal composition has from about 0 percent to about 100 percent of E,E isomers, or from about 0.1 percent to about 50 percent of E,E isomers, or from about 1 percent to about 30 percent of E,E isomers, or from about 2 percent to about 20 percent of E,E isomers, based on the total Z and E isomers in the composition.

The isomeric alkadienal composition has from about 0 percent to about 100 percent of E,Z isomers, or from about 2 percent to about 40 percent of E,Z isomers, or from about 3 percent to about 30 percent of E,Z isomers, or from about 5 percent to about 20 percent of E,Z isomers, based on the total Z and E isomers in the composition.

In accordance with this disclosure, the isomer mixtures of an alkadienal compound can be prepared by reacting an isomeric alkenal compound with a derivative of an alkyltriphenylphosphonium halide compound under reaction conditions sufficient to form an isomer mixture of a derivatized alkadiene compound. The isomer mixture of the derivatized alkadiene compound is then reacted under reaction conditions sufficient to form an alkadienal compound. The alkadienal compound is selected from the group consisting 4,8-undecadienal and isomers thereof, 4,9-dodecadienal and isomers thereof, and 4,10-tridecadienal and isomers thereof.

In an embodiment, the isomeric alkadienals can be prepared by reacting an isomeric alkenal compound with a cyanoalkyltriphenylphosphonium halide compound under reaction conditions sufficient to form an isomer mixture of an alkadienenitrile compound. The isomer mixture of the alkadienenitrile compound is then reacted under reaction conditions sufficient to form an alkadienal compound. This process is exemplified in Examples 1, 3 and 5 hereinbelow and is referred to hereinafter as "Process 1".

Illustrative isomeric alkenal compounds used in the process of this disclosure include, for example, Z-4-heptenal, Z-5-octenal, Z-6-nonenal, and the like. The isomeric alkenal compounds can be used in an amount of from about 5 weight percent to about 10 weight percent, preferably from about 6 weight percent to about 9 weight percent, and more preferably from about 7 weight percent to about 8 weight percent, based on the total weight of the reaction mixture.

Illustrative cyanoalkyltriphenylphosphonium halide compounds used in the process of this disclosure include, for example, (3-cyanopropyl)triphenylphosphonium bromide, and the like. The cyanoalkyltriphenylphosphonium halide compounds can be used in an amount of from about 20 weight percent to about 35 weight percent, preferably from about 25 weight percent to about 30 weight percent, and more preferably from about 26 weight percent to about 28 weight percent, based on the total weight of the reaction mixture.

The cyanoalkyltriphenylphosphonium halide compounds can be prepared by the reaction of a cyanohaloalkyl (e.g., 4-bromobutanenitrile) compound and triphenyl phosphine to form the cyanoalkyltriphenylphosphonium halide compound. This process is exemplified in Examples 3 and 5 hereinbelow.

Illustrative isomer mixtures of the alkadienenitrile compounds used in the process of this disclosure include, for example, isomer mixtures of undecadienenitrile, isomer mixtures of dodecadienenitrile, isomer mixtures of tridecadienenitriles, and the like. The isomer mixtures of the alkadienenitrile compounds can be used in an amount of from about 10 weight percent to about 20 weight percent, preferably from about 12 weight percent to about 18 weight percent, and more preferably from about 14 weight percent to about 16 weight percent, based on the total weight of the reaction mixture.

Other reaction ingredients can be used in amounts sufficient to prepare the isomer mixtures of the alkadienal compounds in accordance with the process of this disclosure.

Illustrative isomer mixtures of alkadienal compounds prepared in accordance with the process of this disclosure include, for example, Z/E isomers of 4,8-undecadienal, Z/E isomers of 4,9-dodecadienal, Z/E isomers of 4,10-tridecadienal and the like. The isomeric mixtures of alkadienals of this disclosure have a Z/E isomer ratio of from about 19:1 to about 2:1 preferably from about 10:2 to about 1.5:0.75 and more preferably from about 5:3 to about 1:1.

With respect to the first step of Process 1, the reaction conditions for the reaction of the alkenal isomer compound with a cyanoalkyltriphenylphosphonium halide compound, such as temperature, pressure and contact time, can vary and any suitable combination of such conditions can be employed herein for preparing the isomer mixture of an alkadienenitrile compound. The reaction temperature can be between about 10° C. to about 100° C., and more preferably between about 20° C. to about 80° C., and most preferably between about 30° C. to about 50° C. Normally, the reaction is carried out under ambient pressure and the contact time can vary from a matter of seconds or minutes to a few hours or greater. The reactants can be added to the reaction mixture or combined in any order. The contact time employed can range from about 0.1 to about 24 hours, preferably from about 0.5 to 15 hours, and more preferably from about 1 to 5 hours.

With respect to the second step of Process 1, the reaction conditions for the reaction of the isomer mixture of the alkadienenitrile compound, such as temperature, pressure and contact time, can vary and any suitable combination of such conditions can be employed herein for preparing the alkadienal compound. The reaction temperature can be between about −10° C. to about −30° C., and more preferably between about −15° C. to about −25° C., and most preferably between about −18° C. to about 20° C. Normally, the reaction is carried out under ambient pressure and the contact time can vary from a matter of seconds or minutes to a few hours or greater. The reactants can be added to the reaction mixture or combined in any order. The contact time employed can range from about 0.1 to about 24 hours, preferably from about 0.5 to 15 hours, and more preferably from about 1 to 5 hours.

In accordance with this disclosure, the isomer mixtures of an alkadienal compound can also be prepared by reacting a derivative of an isomeric alkadiene compound in the presence of an isomerizing agent under reaction conditions sufficient to form an isomer mixture of the derivative of the alkadiene compound. The isomer mixture of the derivative of the alkadiene compound is then reacted in the presence of a reducing agent under reaction conditions sufficient to form an isomer mixture of an alkadienal compound. The alkadienal compound is selected from the group consisting 4,8-undecadienal and isomers thereof, 4,9-dodecadienal and isomers thereof, and 4,10-tridecadienal and isomers thereof.

In particular, the isomeric alkadienals can be prepared by reacting an isomeric alkadienenitrile compound in the presence of an isomerizing agent under reaction conditions sufficient to form an isomer mixture of an alkadienenitrile compound. The isomer mixture of the alkadienenitrile compound is then reacted in the presence of a reducing agent under reaction conditions sufficient to form an isomer mixture of an alkadienal compound. This process is exemplified in Examples 2, 4 and 6 hereinbelow and is referred to hereinafter as "Process 2".

Illustrative isomer mixtures of the alkadienenitrile compounds and reducing agents are described above. Illustrative isomer mixtures of alkadienal compounds prepared in accordance with the process of this disclosure are described above.

Illustrative isomeric alkadienenitrile compounds used in the process of this disclosure include, for example, isomeric undecadienenitrile, isomeric dodecadienenitrile, isomeric tridecadienenitriles, and the like. The isomeric alkadienenitrile compounds can be used in an amount of from about 90 weight percent to about 98 weight percent, preferably from about 92 weight percent to about 96 weight percent, and more preferably from about 93 weight percent to about 95 weight percent, based on the total weight of the reaction mixture.

Illustrative isomerizing agents used in the process of this disclosure include, for example, aromatic acids such as p-toluenesulfinic acid, and the like. The isomerizing agents can be used in an amount of from about 0.5 weight percent to about 4 weight percent, preferably from about 0.75 weight percent to about 3 weight percent, and more preferably from about 1 weight percent to about 2 weight percent, based on the total weight of the reaction mixture.

Illustrative reducing agents used in the process of this disclosure include, for example, diisobutylaluminum hydride (DIBAL), and the like. The reducing agents can be used in an amount of from about 10 weight percent to about 18 weight percent, preferably from about 12 weight percent to about 15 weight percent, and more preferably from about 13 weight percent to about 14 weight percent, based on the total weight of the reaction mixture.

Other reaction ingredients can be used in amounts sufficient to prepare the isomer mixtures of the alkadienal compounds in accordance with the process of this disclosure.

With respect to the first step of Process 2, the reaction conditions for the reaction of the isomeric alkadienenitrile compound in the presence of an isomerizing agent, such as temperature, pressure and contact time, can vary and any suitable combination of such conditions can be employed herein for preparing the isomer mixture of an alkadienenitrile compound. The reaction temperature can be between about 80° C. to about 110° C., and more preferably between about 85° C. to about 105° C., and most preferably between about 90° C. to about 100° C. Normally, the reaction is carried out under ambient pressure and the contact time can vary from a matter of seconds or minutes to a few hours or greater. The reactants can be added to the reaction mixture or combined in any order. The contact time employed can range from about 0.1 to about 24 hours, preferably from about 0.5 to 15 hours, and more preferably from about 1 to 5 hours.

With respect to the second step of Process 2, the reaction conditions for the reaction of the isomer mixture of the alkadienenitrile compound in the presence of a reducing agent, such as temperature, pressure and contact time, can vary and any suitable combination of such conditions can be employed herein for preparing the isomer mixture of an alkadienal compound. The reaction temperature can be between about −10° C. to about −30° C., and more preferably between about −15° C. to about −25° C., and most preferably between about −18° C. to about −20° C. Normally, the reaction is carried out under ambient pressure and the contact time can vary from a matter of seconds or minutes to a few hours or greater. The reactants can be added to the reaction mixture or combined in any order. The contact time employed can range from about 0.1 to about 24 hours, preferably from about 0.5 to 15 hours, and more preferably from about 1 to 5 hours.

In accordance with this disclosure, it has been found that 4,8-undecadienal isomers, 4,9-dodecadienal isomers, and 4,10-tridecadienal isomers, when compared with 4,7-decadienal, possesses different odor character and greater odor intensity. The 4,8-undecadienal isomers, 4,9-dodecadienal isomers, and 4,10-tridecadienal isomers represented a much broader range of odor notes, particularly being fresh, citrus, ozonic and much less fatty and aldehydic than 4,7-decadienal. Overall, both cis,cis and mixed isomers had strong odor intensity. See, for example, FIG. 1 which lists odor description and strength for Z,Z-4,7-decadienal, Z,Z-4,8-undecadienal, mixed (Z & E) 4,8-undecadienal, Z,Z-4,9-dodecadienal, mixed (Z & E) 4,9-dodecadienal, Z,Z-4,10-tridecadienal and mixed (Z & E) 4,10-tridecadienal. It is surprising that the odor intensity does not significantly diminish as one goes up the homologous series.

The general understanding is that the odor intensity declines as one ascends a homologous series. For example, it has been found that cis-4-decenal is much more powerful than its higher homologs, e.g., cis-4-undecenal, cis-4-dodecenal and cis-4-tridecenal. With this established pattern, it was surprising to observe that the introduction of a second double bond reverses this trend, e.g., 4,7-decadienal<4,8-undecadienal<4,9-dodecadienal<4,10-tridecadienal.

The compounds of this disclosure can be used in a broad range of fragrance applications, e.g., fine fragrances, household products, laundry products, personal care products and cosmetics. These compounds can be employed in widely varying amounts, depending upon the specific application and on the nature and amounts of other odor carrying ingredients. But because of the exceptional strength of these materials, the odor effect can be achieved at a very low level of incorporation.

Fragrances in consumer products provide several functions. They mask base odors, provide aesthetic pleasure and signal product attributes and function to the user, e.g., hygiene, cleanliness, mildness. Notwithstanding these benefits, it is also true that perfumes can cause a myriad of problems within products they have been added to, e.g., discoloration, phase separation, problems such as irritation and occasional allergic reaction to the user. Additionally, fragrances represent one of the more expensive components of the product and many fragrance ingredients may not be easily biodegradable. Over the years, perfume levels in many consumer products have increased by the popular demand but at the same time consumers have also become more critical of the fragranced products they purchase and use.

Therefore, an embodiment of this disclosure is to provide high intensity consumer acceptable fragrances and desirable hedonics at a much lower concentration than achieved before. This lowering of fragrance concentration in consumer products by an order of magnitude has the benefit of cost saving, less interference with the physical properties of the product base, minimizing toxicological implications on the user, and lowering the environmental impact of chemicals used.

As used herein, the expression "perfume composition" means a mixture of fragrance materials and possibly auxiliary substances, if desired dissolved in a suitable solvent or mixed with a powdery substrate which is used to impart a desired odor to the skin and/or all types of products. Examples of such products include soaps, detergents, air fresheners, room sprays, pomanders, candles, cosmetics, such as creams, ointments, toilet waters, pre- and aftershave lotions, talcum powders, hair-care agents, body deodorants and anti-perspirants.

Fragrance materials and mixtures of fragrance materials which can be used in combination with the compounds according to this disclosure for manufacturing perfume compositions are, for example, natural products, such as essential oils, absolutes, resinoids, resins, concretes etc, but also synthetic fragrance materials such as hydrocarbons, alcohols, aldehydes, ketones, ethers, acids, esters, acetals, ketals, nitriles etc, including saturated and unsaturated compounds, aliphatic carbocyclic and heterocyclic compounds.

Examples of fragrance materials which can be used in combination with the compounds according to the disclosure include geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexyl-cinnam-aldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentanone, 2-n-heptylcyclopentanone, 3-methyl-2-pentyl-2-cyclopentenone, n-decanal, n-dodecanal, 9-decen-1-01, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, aromatic nitromusks, and the like.

Auxiliary substances and solvents which can be used in perfume compositions which contain compounds according to this disclosure include, for example: ethanol, isopropanol, dipropylene glycol, dipropyleneglycol monomethyl ether, diethylphthalate, and the like.

The quantities in which the compounds according to this disclosure can be used in perfume compositions or in products to be perfumed can vary within wide limits and depend inter alia on the nature of the product in which the fragrance material is used, on the nature and quantity of the other components in the perfume composition and on the odor effect which is aimed at. It is therefore only possible to specify very rough limits, which, however, provide sufficient information for the specialist to be able to use the compounds according to the disclosure independently. In most cases a quantity of only 1 ppm in a perfume composition will already be sufficient to obtain a clearly perceptible odor effect. On the other hand, to achieve special odoriferous effects it is possible to use quantities of 100, 1000, 5000 ppm or even more in a composition. In products perfumed with such compositions these concentrations are proportionately lower, depending on the quantity of composition used in the product.

There are three basic stages of a fragrance. The first stage (i.e., top notes) is the first impression that a fragrance gives to a customer. This initial stage is the most volatile. In the second stage (i.e., middle notes), a few moments after the application of a fragrance, the heart is revealed. This modifying part of the fragrance has medium volatility. In the third stage (i.e., base notes), after a fragrance dries down, these notes are more pronounced. This part of the fragrance is the longest lasting. The balance between these three groups is very important. In a well balanced fragrance, it is important to understand what group or groups are the most important for a particular application. The fragrance compositions of this disclosure exemplify a desirable balance between these three groups for desired applications.

The following examples are only to illustrate the preparation and use of the compounds according to the disclosure. The disclosure is not limited thereto.

EXAMPLES

Example 1

Preparation of Z,Z-4,8-undecadienal

A. Preparation of Z,Z-4,8-undecadienenitrile

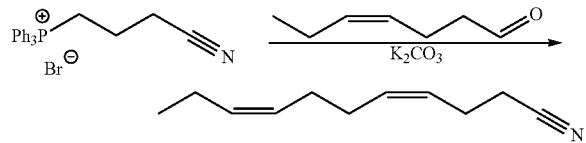

Z-4-heptenal (168.3 grams, 1.5 mol, 1.0 eq.) was fed during 4 hours to stirred mixture of (3-cyanopropyl)triphenylphosphonium bromide (615.4 grams, 1.5 mol, 1.0 eq.) and anhydrous potassium carbonate (414.6 grams, 3.0 mol, 2.0 eq.) in DMF (1000 milliliters) at 100° C. Mixture was stirred at 100° C. for additional 2.5 hours, left overnight at room temperature, diluted with water (1 L) and methanol (500 milliliters) and extracted with heptane (5×300 milliliters). Solvent was removed under reduced pressure and residue was distilled (0.5 Torr, 100-105° C.) to give product as colorless liquid (200.2 grams, yield 78.5%, purity 96.0%). Isomers: Z,Z 90.0%, E,Z 7.5%, Z,E 2.3%, E,E 0.2%.

B. Preparation of Z,Z-4,8-undecadienal

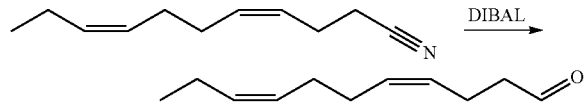

Z,Z-4,8-undecadienenitrile (96.0% pure, 10.0 grams, 0.059 mol, 1.0 eq.) in toluene (20 milliliters) was cooled to −20° C. and DIBAL (25% solution in toluene, 36.8 grams, 0.065 mol, 1.1 eq.) was added dropwise during 1 hour maintaining temperature between −15° C. and −20° C. Mixture was warmed slowly to room temperature, stirred for 1 hour, cooled to 0° C. and quenched with methanol (10 milliliters). Clear solution was poured into mixture of concentrated hydrochloric acid (50 milliliters) and water (150 milliliters). Organic layer was separated, washed with 1M hydrochloric acid, brine, saturated aqueous sodium hydrogen carbonate and brine. Solvent was removed under reduced pressure. Residue was distilled (0.5 Torr, 70-75° C.) to give Z,Z-4,8-undecadienal (6.9 grams, yield 69.0%, purity 97.8%) as colorless liquid.

Example 2

Preparation of isomerized 4,8-undecadienal

A. Preparation of isomerized 4,8-undecadienenitrile

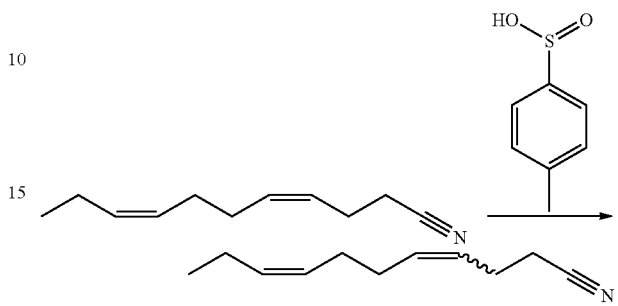

Z,Z-4,8-undecadienenitrile (96.0% pure, 10.0 grams, 0.059 mol, 1.0 eq.) was heated with p-toluenesulfinic acid (0.92 grams, 0.006 mol, 0.1 eq.) at 100° C. for 1 hour. Mixture was cooled, diluted with heptane (100 milliliters), washed with saturated aqueous sodium hydrogen carbonate (3×), water (2×) and dried with anhydrous sodium sulfate. Solvent was removed under reduced pressure. Residue was distilled (0.5 Torr, 100-105° C.) to give 4,8-undecadienenitrile (8.2 grams, yield 83.3%, purity 97.5%) as colorless liquid. Isomers: Z,Z 45.1%, E,Z 17.6%, Z,E 25.4%, E,E 11.9%.

B. Preparation of isomerized 4,8-undecadienal

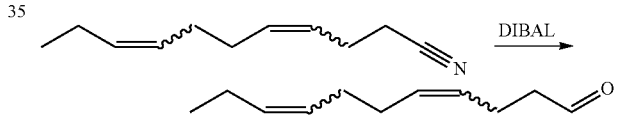

Isomerized 4,8-undecadienenitrile (97.5% pure, 10.0 grams, 0.06 mol, 1.0 eq.) in toluene (20 milliliters) was cooled to −20° C. and DIBAL (25% solution in toluene, 37.4 grams, 0.066 mol, 1.1 eq.) was added dropwise during 1 hour maintaining temperature between −15° C. and −20° C. Mixture was warmed slowly to room temperature, stirred for 1 hour, cooled to 0° C. and quenched with methanol (10 milliliters). Clear solution was poured into mixture of concentrated hydrochloric acid (50 milliliters) and water (150 milliliters). Organic layer was separated, washed with 1M hydrochloric acid, brine, saturated aqueous sodium hydrogen carbonate and brine. Solvent was removed under reduced pressure. Residue was distilled (0.5 Torr, 70-75° C.) to give 4,8-undecadienal (6.8 grams, yield 67.3%, purity 98.3%) as colorless liquid.

Example 3

Preparation of Z,Z-4,9-dodecadienal

A. Preparation of Z,Z-4,9-dodecadienenitrile

-continued

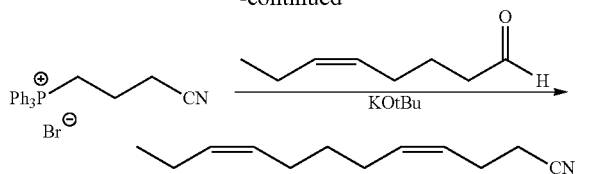

A mixture of 4-bromobutanenitrile (130.3 grams, 0.88 mol) and triphenylphosphine (239.4 grams, 0.91 mol) in diglyme (261 milliliters) was heated at 95° C. for 17.3 hours. The mixture was cooled to 90° C., then THF (379 milliliters) was added. The resulting mixture was cooled in an ice bath. Potassium tert-butoxide (105.8 grams) was then added in 10 gram portions. After 90 minutes, a solution of Z-5-octenal (104.7 grams, 0.83 mol) in THF (120 milliliters) was added slowly. 45 minutes after completion of the feed the mixture was removed from the ice bath and quenched with water (345 milliliters). After stirring for 5 minutes, the layers were separated. The solvents and lights were distilled from the mixture on a fractionating column ultimately taking the pot to 62° C. at 100 mmHg. After cooling, the liquid remaining in the pot was thoroughly mixed with methanol (319 milliliters), water (371 milliliters) and heptane (559 milliliters). The bottom two layers were drained together and saved. The top layer was also saved separately. The bottom two layers were diluted with methanol (157 milliliters) then extracted 3× with the following quantities of heptane (363 milliliters, 274 milliliters and 194 milliliters). All of the heptane extracts were combined then distilled on a fractionating column at reduced pressure (b.p. 77° C. at 0.2 mmHg) to give Z,Z-4,9-dodecadienenitrile (94.3 grams) as colorless liquid. Isomeric purity ~91% Z,Z.

B. Preparation of Z,Z-4,9-dodecadienal

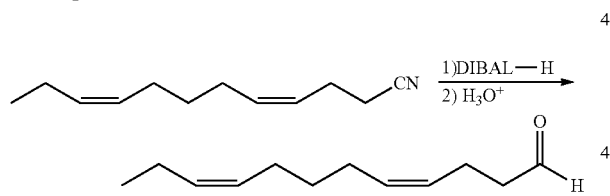

A round-bottomed flask was charged with Z,Z-4,9-dodecadienenitrile (83.1 grams, 0.469 mol) and toluene (322 milliliters). To the stirred solution, DIBAL-H (1.5 M in toluene, 279.7 grams) was added slowly maintaining the reaction temperature between 6 and 24° C. with an ice bath. After stirring for 2 hours, ethyl acetate (5.6 milliliters) was added. After stirring for another 10 minutes, the reaction was added to a stirred solution of 5M HCl (801 grams) maintaining the temperature between 25 and 35° C. Once all of the feed was in, the mixture was diluted with THF (225 milliliters). The layers were separated. The organic layer was washed with a solution of NaCl (16 grams) and 10M HCl (53 grams) in water (107 grams). Then 2× with 10% dipotassium phosphate (120 grams each wash). The organic layer was vacuum distilled (b.p. 70° C. at 0.2 mmHg) on a fractionating column to give Z,Z-4,9-dodecadienal (17.2 grams) as colorless liquid.

Example 4

Preparation of isomerized 4,9-dodecadienal

A. Preparation of isomerized 4,9-dodecadienenitrile

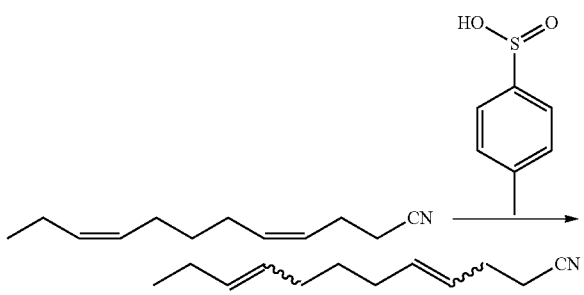

Z,Z-4,9-dodecadienenitrile (124.1 grams, 0.70 mol) was heated with p-toluenesulfinic acid (1.10 grams, 7 mmol) at 145-150° C. for 3.9 hours. Additional p-toluenesulfinic acid was added after 1.2 hours and 2.7 hours (1.08 grams and 1.10 grams, respectively). The mixture was cooled, diluted with CPME (130 milliliters) and ethanol (25 milliliters), washed with 5% NaOH (100 grams) then with 5% sodium hydrogen carbonate (100 grams). The organic layer was fractionally distilled (b.p. 82° C. at 0.3 mmHg) to give 4,9-dodecadienenitrile (90.7 grams) as colorless liquid. Isomer ratio: 4E,9E 36.1%, 4Z,9E 36.2%, 4E,9Z 13.5%, 4Z,9Z 14.2%.

B. Preparation of isomerized 4,9-dodecadienal

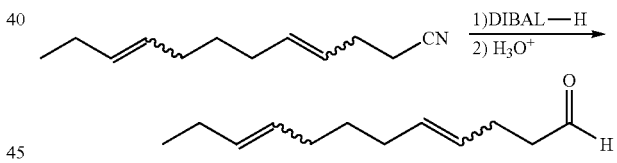

A round-bottomed flask was charged with 4,9-dodecadienenitrile isomer mix (88.88 grams, 0.501 mol) and toluene (355 milliliters). To the stirred solution, DIBAL-H (1.5 M in toluene, 303 grams) was added slowly maintaining the reaction temperature between 4 and 18° C. with an ice bath. After stirring for 2.8 hours, ethyl acetate (5 milliliters) was added. After stirring for another 0.3 hours, the reaction was added to a stirred solution of 5M HCl (869 grams) maintaining the temperature between 25 and 35° C. Added THF (40 milliliters). After thorough mixing, the layers were separated. The organic layer was washed with a solution of 3M HCl (210 grams), then 2× with 20% dipotassium phosphate (150 grams). The organic layer was vacuum distilled (b.p. 72° C. at 0.2 mmHg) on a fractionating column to give 4,9-dodecadienal isomer mix (21.9 grams) as colorless liquid. The isomers could not be resolved by GC, but it can be assumed to have an isomer composition similar to that of the starting nitrile.

Example 5

Preparation of Z,Z-4,10-tridecadienal

A. Preparation of Z,Z-4,10-tridecadienenitrile

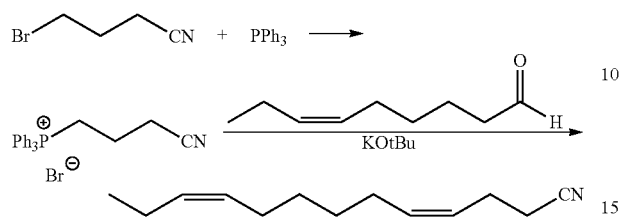

A mixture of 4-bromobutanenitrile (265.1 grams, 1.79 mol) and triphenylphosphine (492 grams, 1.88 mol) in diglyme (530 milliliters) was heated at 95° C. for 23.3 hours. The mixture was cooled to 90° C., then THF (706 milliliters) was added. The resulting mixture was cooled in an ice bath. Potassium tert-butoxide (201.3 grams) was then added in 20 gram portions. After 2 hours, a solution of Z-6-nonenal (239.3 grams, 1.71 mol) in THF (285 milliliters) was added slowly. 5 minutes after completion of the feed the mixture was removed from the ice bath. After warming to ambient temperature overnight, the reaction was quenched with water (703 milliliters). After stirring for 10 minutes, the layers were separated. The solvents and lights were distilled from the mixture on a fractionating column ultimately taking the pot to 60° C. at 100 mmHg. After cooling, the liquid remaining in the pot was thoroughly mixed with methanol (631 milliliters), water (740 milliliters) and heptane (559 milliliters). The bottom two layers were drained together and saved. The top layer was also saved separately. The bottom two layers were diluted with methanol (316 milliliters) then extracted 2× with the following quantities of heptane (721 milliliters and 544 milliliters). All of the heptane extracts were combined then distilled on a fractionating column at reduced pressure (b.p. 90° C. at 0.2 mmHg) to give Z,Z-4, 10-tridecadienenitrile (241.1 grams) as colorless liquid. Isomeric purity ~92% Z,Z.

B. Preparation of Z,Z-4,10-tridecadienal

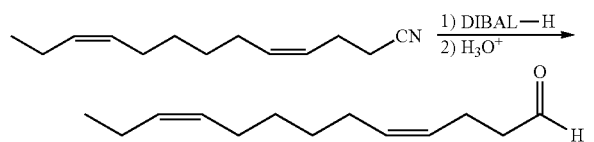

A round-bottomed flask was charged with Z,Z-4,10-tridecadienenitrile (108.4 grams, 0.567 mol) and toluene (395 milliliters). To the stirred solution, DIBAL-H (1.5 M in toluene, 342.9 grams) was added slowly maintaining the reaction temperature between 7 and 26° C. with an ice bath. After stirring for 1.4 hours, ethyl acetate (5.6 milliliters) was added. After stirring for another 10 minutes, the reaction was added to a stirred solution of 5M HCl (998 grams) maintaining the temperature between 25 and 35° C. After thorough mixing, the layers were separated. The organic layer was washed with a solution of 3M HCl (200 grams), then 4× with 10% dipotassium phosphate (160 grams each wash). The organic layer was vacuum distilled (b.p. 85° C. at 0.2 mmHg) on a fractionating column to give Z,Z-4,10-tridecadienal (22.7 grams) as colorless liquid.

Example 6

Preparation of isomerized 4,10-tridecadienal

A. Preparation of isomerized 4,10-tridecadienenitrile

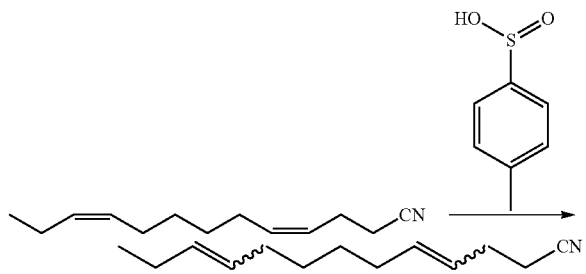

Z,Z-4,10-tridecadienenitrile (130.1 grams, 0.68 mol) was heated with p-toluenesulfinic acid (1.25 grams, 8 mmol) at 145-150° C. for 3.1 hour. Additional p-toluenesulfinic acid was added after 0.8 hours and 1.5 hours (0.33 grams and 0.32 grams, respectively). The mixture was cooled, diluted with heptane (150 milliliters) and THF (11 milliliters), washed with 5% NaOH (100 grams) then with 5% sodium hydrogen carbonate (100 grams). The organic layer was fractionally distilled (b.p. 97° C. at 0.3 mmHg) to give 4,10-tridecadienenitrile (105 grams) as colorless liquid. Isomer ratio: 4E,10E 46.3%, isomer 2 31.6%, isomer 3 12.8%, 4Z,10Z 9.2%.

B. Preparation of isomerized 4,10-tridecadienal

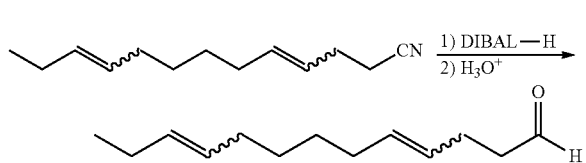

A round-bottomed flask was charged with 4,10-tridecadienenitrile isomer mix (104.1 grams, 0.544 mol) and toluene (380 milliliters). To the stirred solution, DIBAL-H (1.5 M in toluene, 327 grams) was added slowly maintaining the reaction temperature between 5 and 23° C. with an ice bath. After stirring for 2.4 hours, ethyl acetate (5.6 milliliters) was added. After stirring for another 0.7 hours, the reaction was added to a stirred solution of 5M HCl (941 grams) maintaining the temperature between 25 and 35° C. After thorough mixing, the layers were separated. The organic layer was washed with a solution of 3M HCl (190 grams), then 1× with saturated NaCl, 1× with 10% dipotassium phosphate (150 grams) then 2× with 20% dipotassium phosphate (150 grams). The organic layer was vacuum distilled (b.p. 85° C. at 0.2 mmHg) on a fractionating column to give 4,10-tridecadienal isomer mix (35.1 grams) as colorless liquid. The isomers could not be resolved, but it can be assumed to have an isomer composition similar to that of the starting nitrile.

Example 7

Preparation of Sun Dried Linen Perfume Formulation

A perfume composition of the sun dried linen type for use in laundry detergent was prepared to demonstrate that the addition of z,z-4,8-undecadienal and 4,10-tridecadienal according to the formulation described below provided a bright, fresh, ozonic, crisp clean odor.

Sun Dried Linen Perfume

| | |
|---|---|
| Acet Aldehyde DMA 10% | 50 |
| Amyl Acetate | 20 |
| Aurantiol | 15 |
| Benzyl Acetate | 50 |
| Benzyl Alcohol | 10 |
| Benzyl Salicylate | 25 |
| Cetalox 1% | 20 |
| Clove Oil Madagascar | 25 |
| Damascene Alpha 10% | 20 |
| Dipropylene Glycol | 90 |
| Galbex 183 | 15 |
| Globanone 50% IPM | 285 |
| Heliopropanal | 55 |
| Hexyl Cinn Aldehyde | 420 |
| Hyacinth Body | 10 |
| Indomethylene | 5 |
| Iso Cyclo Citral 1% | 40 |
| Iso E Super | 35 |
| Lilial | 385 |
| Linalol | 90 |
| Linalyl Acetate | 15 |
| Methoxy Melonal 10% | 10 |
| Methyl Ionone Gamma | 55 |
| Patchouli Oil | 20 |
| Phenyl Ethyl Acetate | 40 |
| Phenyl Ethyl Alcohol | 210 |
| Phenyl Ethyl Dimethyl Carbinol | 20 |
| Phenyl Ethyl Methyl Ether 10% | 10 |
| Prunella 10% | 30 |
| Rose Oxide 10% | 20 |
| Rosinol Cryst 10% | 60 |
| Styrax Purif 50% | 10 |
| Tonalide | 280 |
| Triplal 10% | 25 |
| Undecalactone Gamma 10% | 60 |
| Verdox | 30 |
| Verdyl Acetate | 105 |
| Vertenex | 165 |
| Ylang Syn | 25 |
| Z,Z-4,8-undecadienal 0.1% | 110 |
| Z,Z-4,10-tridecadienal 0.1% | 10 |
| Z-4-Undecenal 10% | 25 |
| Total | 3000 |

Example 8

Preparation of Fruity Floral Type Formulation

A perfume formulation of fruity floral type using z,z-4,8-undecadienal and z,z-4,9-dodecadienal was prepared for use in shampoo. The formulation is described below.

Fruity Floral Perfume

| | |
|---|---|
| Acetophenone 10% | 5 |
| 2,3 Pentadione 10% | 7 |
| Aldehyde C-16 | 126 |
| Benzyl Aldehyde 10% | 7 |
| Benzyl Acetate | 7 |
| Cinnamon Leaf Oil | 6 |
| Cis-3-Hexenyl Acetate | 4 |
| Dimethyl Benzyl Carb Acetate | 3 |
| Ethyl Acetate | 33 |
| Ethyl Aceto Acetate | 89 |
| Ethyl Butyrate | 11 |
| Galaxolide 50 BB | 62 |
| Decalactone Gamma | 19 |
| Undecalactone Gamma | 59 |
| Dipropylene Glycol | 273 |

-continued

| | |
|---|---|
| Hexyl Acetate 10% | 17 |
| Hexyl Cinnamic Aldehyde | 7 |
| Linalol | 8 |
| Z,Z-4,8-undecadienal 1% | 23 |
| Orange Oil | 8 |
| Phenyl Ethyl Isobutyrate | 8 |
| Vanillin | 39 |
| Veltol Plus | 47 |
| Verdox | 82 |
| 3-Hexenal mixture 1% (triacetin) | 30 |
| Z,Z-4,9-dodecadienal 0.01% | 20 |
| Total | 1000 |

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. A composition comprising an alkadienal selected from the group consisting of 4,8-undecadienal and isomers thereof, 4,9-dodecadienal and isomers thereof, and 4,10-tridecadienal and isomers thereof, wherein said composition is a fragrance composition or a flavor composition.

2. The composition of claim 1 wherein the isomers of 4,8-undecadienal comprise Z,Z-4,8-undecadienal, E,E-4,8-undecadienal, and mixed Z/E isomers of 4,8-undecadienal; the isomers of 4,9-dodecadienal comprise Z,Z-4,9-dodecadienal, E,E-4,9-dodecadienal, and mixed Z/E isomers of 4,9-dodecadienal; and the isomers of 4,10-tridecadienal comprise Z,Z-4,10-tridecadienal, E,E-4,10-tridecadienal, and mixed Z/E isomers of 4,10-tridecadienal.

3. The composition of claim 1 wherein the isomers of 4,8-undecadienal have double bonds with a Z/E isomer ratio of from about 30:1 to about 1:30; the isomers of 4,9-dodecadienal have double bonds with a Z/E isomer ratio of from about 30:1 to about 1:30; and the isomers of 4,10-tridecadienal have double bonds with a Z/E isomer ratio of from about 30:1 to about 1:30.

4. The composition of claim 1 wherein the isomers of 4,8-undecadienal have double bonds with a Z/E isomer ratio of from about 12:1 to about 1:12; the isomers of 4,9-dodecadienal have double bonds with a Z/E isomer ratio of from about 12:1 to about 1:12; and the isomers of 4,10-tridecadienal have double bonds with a Z/E isomer ratio of from about 12:1 to about 1:12.

5. The composition of claim 1 wherein the isomers of 4,8-undecadienal have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; the isomers of 4,9-dodecadienal have from about 5 percent to about 95 percent of Z,Z isomers, from about 0.5percent to about 90 percent of Z,E isomers, from about 0.1 percent to about 50percent of E,E isomers, and from about 2 percent to about 40 percent of E,Z isomers; the isomers of 4,10-tridecadienal have from about 5 percent to about 95 percent of Z,Z isomers, from about 0.5 percent to about 90 percent of Z,E isomers, from about 0.1 percent to about 50percent of E,E isomers, and from about 2 percent to about 40 percent of E,Z isomers; all based on the total Z and E isomers in the composition.

6. The composition of claim 1 wherein the isomers of 4,8-undecadienal are present in an amount of at least 1 ppm by weight, based on the total weight of the composition; the isomers of 4,9-dodecadienal are present in an amount of at least 1 ppm by weight, based on the total weight of the composition; and the isomers of 4,10-tridecadienal are present in an amount of at least 1 ppm by weight, based on the total weight of the composition.

7. A perfume composition comprising an effective amount of at least one alkadienal selected from the group consisting of 4,8-undecadienal and isomers thereof, 4,9-dodecadienal and isomers thereof, and 4,10-tridecadienal and isomers thereof.

8. The perfume composition of claim 7 wherein the isomers of 4,8-undecadienal comprise Z,Z-4,8-undecadienal, E,E-4,8-undecadienal, and mixed Z/E isomers of 4,8-undecadienal; the isomers of 4,9-dodecadienal comprise Z,Z-4,9-dodecadienal, E,E-4,9-dodecadienal, and mixed Z/E isomers of 4,9-dodecadienal; and the isomers of 4,10-tridecadienal comprise Z,Z-4 10-tridecadienal, E,E-4,10-tridecadienal, and mixed Z/E isomers of 4,10-tridecadienal.

9. The perfume composition of claim 7 wherein the isomers of 4,8-undecadienal have double bonds with a Z/E isomer ratio of from about 30:1 to about 1:30; the isomers of 4,9-dodecadienal have double bonds with a Z/E isomer ratio of from about 30:1 to about 1:30; and the isomers of 4,10-tridecadienal have double bonds with a Z/E isomer ratio of from about 30:1 to about 1:30.

10. The perfume composition of claim 7 wherein the isomers of 4,8-undecadienal have double bonds with a Z/E isomer ratio of from about 12:1 to about 1:12; the isomers of 4,9-dodecadienal have double bonds with a Z/E isomer ratio of from about 12:1to about 1:12; and the isomers of 4,10-tridecadienal have double bonds with a Z/E isomer ratio of from about 12:1 to about 1:12.

11. The perfume composition of claim 7 wherein the isomers of 4,8-undecadienal have from about 5 percent to about 95 percent of Z,Z isomers, from about 0.5 percent to about 90percent of Z,E isomers, from about 0.1 percent to about 50 percent of E,E isomers, and from about 2 percent to about 40 percent of E,Z isomers; the isomers of 4,9-dodecadienal have from about 5 percent to about 95 percent of Z,Z isomers, from about 0.5 percent to about 90 percent of Z,E isomers, from about 0.1 percent to about 50 percent of E,E isomers, and from about 2 percent to about 40 percent of E,Z isomers; the isomers of 4,10-tridecadienal have from about 5 percent to about 95 percent of Z,Z isomers, from about 0.5 percent to about 90 percent of Z,E isomers, from about 0.1 percent to about 50percent of E,E isomers, and from about 2 percent to about 40 percent of E,Z isomers; all based on the total Z and E isomers in the composition.

12. The perfume composition of claim 7 wherein the isomers of 4,8-undecadienal are present in an amount of at least 1 ppm by weight, based on the total weight of the composition; the isomers of 4,9-dodecadienal are present in an amount of at least 1 ppm by weight, based on the total weight of the composition; and the isomers of 4,10-tridecadienal are present in an amount of at least 1 ppm by weight, based on the total weight of the composition.

13. The perfume composition of claim 7 further comprising one or more of geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnam- aldehyde, 2-methyl-3-(p-tert-butylpheityl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl- tetrahydropyran, 3-carboxymethyl-2-pentylcyclopentanone, 2-n-heptylcyclopentanone, 3-methyl-2-pentyl-2-cyclopentenone, n-decanal, n-dodecanal, 9-decen-1-01, phenoxyethylisobutyrate, phenylacetaldehydedi-methylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indan-musks, tetraline-musks, isochromane-musks, macrocyclic ketones, macrolactone-musks, ethylene brassylate, and aromatic nitromusks.

14. An alkadienal compound selected from the group consisting of 4,8-undecadienal and isomers thereof, 4,9-dodecadienal and isomers thereof, and 4,10-tridecadienal and isomers thereof, wherein said alkadienal compound is a fragrance compound or a flavor compound.

\* \* \* \* \*